United States Patent [19]

Prahl

[11] Patent Number: 5,537,764
[45] Date of Patent: Jul. 23, 1996

[54] FOREFOOT RELIEF SHOE

[75] Inventor: Jan E. M. Prahl, Rullstorf, Germany

[73] Assignee: Heil- und Hilfsmittel Vertriebs GmbH, Scharnebek, Germany

[21] Appl. No.: 328,877

[22] Filed: Oct. 25, 1994

[30] Foreign Application Priority Data

Jul. 21, 1994 [DE] Germany ............................ 9411782 U

[51] Int. Cl.⁶ ................................. A43B 7/14; A43B 3/12
[52] U.S. Cl. ........................... 36/110; 36/11.5; 36/25 R; 602/23
[58] Field of Search ............................ 36/110, 81, 11.5, 36/25 R; 602/23

[56] References Cited

U.S. PATENT DOCUMENTS

| 3,061,951 | 11/1962 | Barron | 36/7.8 |
| 3,859,727 | 1/1975 | Nakamoto | 36/11.5 |
| 4,020,569 | 5/1977 | Fukuoka | 36/11.5 |
| 4,546,557 | 10/1985 | Barouk et al. | |
| 4,567,678 | 2/1986 | Morgan et al. | 36/110 |
| 4,726,127 | 2/1988 | Barouk | 36/110 |
| 5,078,128 | 1/1992 | Grim et al. | 602/23 |
| 5,088,481 | 2/1992 | Darby | 36/110 |
| 5,138,777 | 8/1992 | Darby | 36/110 |

FOREIGN PATENT DOCUMENTS

| 2489103 | 3/1982 | France | 36/11.5 |
| 2210559 | 6/1989 | United Kingdom | 602/23 |

*Primary Examiner*—Paul T. Sewell
*Assistant Examiner*—Marie Denise Patterson
*Attorney, Agent, or Firm*—Friedrich Kueffner

[57] ABSTRACT

The invention relates to a forefoot relief shoe (10) possessing a sole portion (11) that is substantially triangular in a side view or in a vertical longitudinal section having a thickness which decreases in the rearward direction and which terminates anteriorly before the the metatarsal region of the wearer. In order to increase the service life and to enhance the wearing comfort it is provided that the sole portion (11) is constructed in the form of a hollow section fitted with substantially vertical supports for connecting the base constructed so as to cover the area to its full extent and the upper body (12) constructed so as to cover the area to its full extent and adjacent to the foot bed (13), in which case the supports, at least within the central area, in the longitudinal axial direction toward the base, possess an increasing diameter or an increasing horizontal cross-section (FIG. 1)

8 Claims, 6 Drawing Sheets

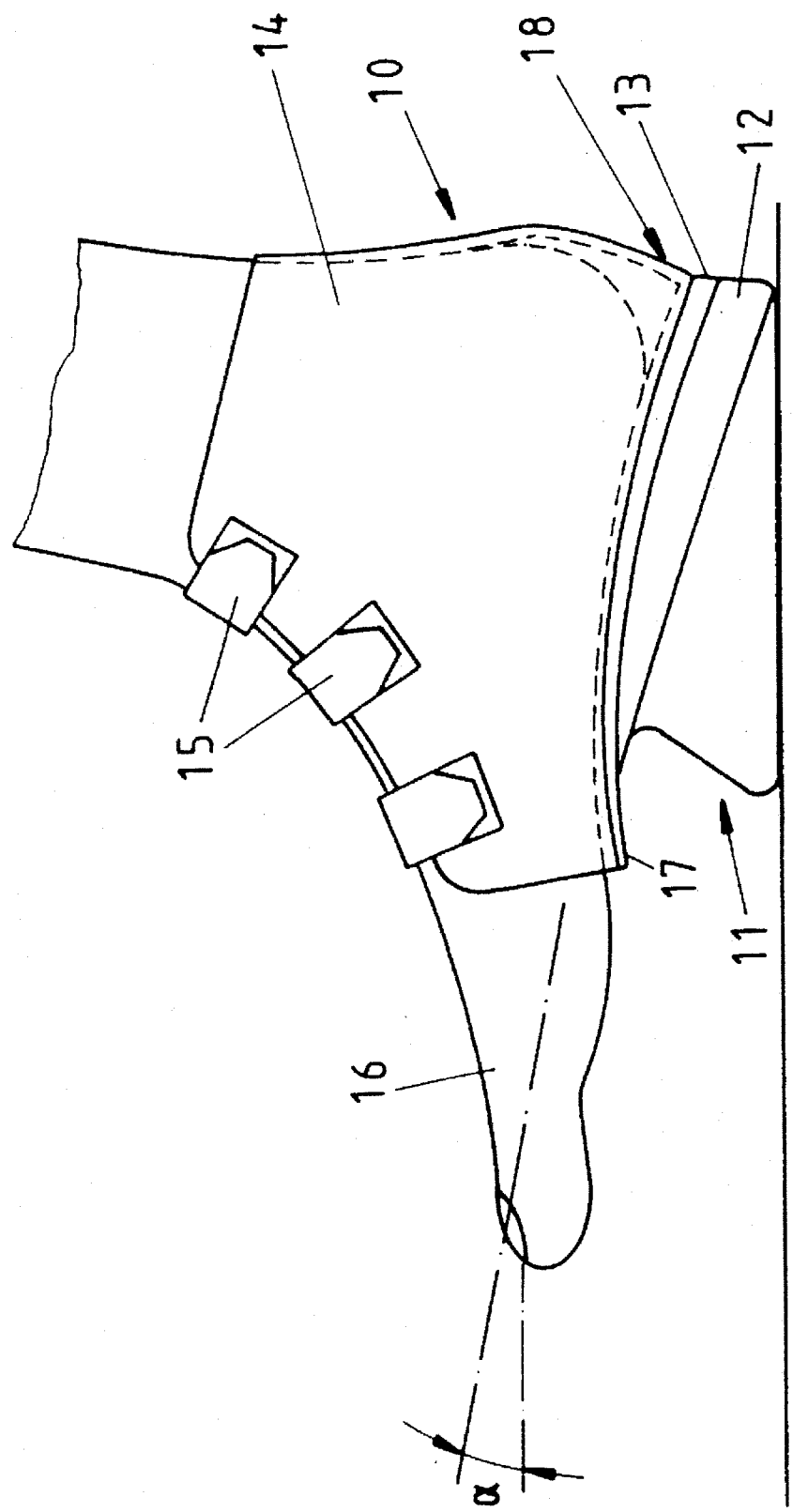

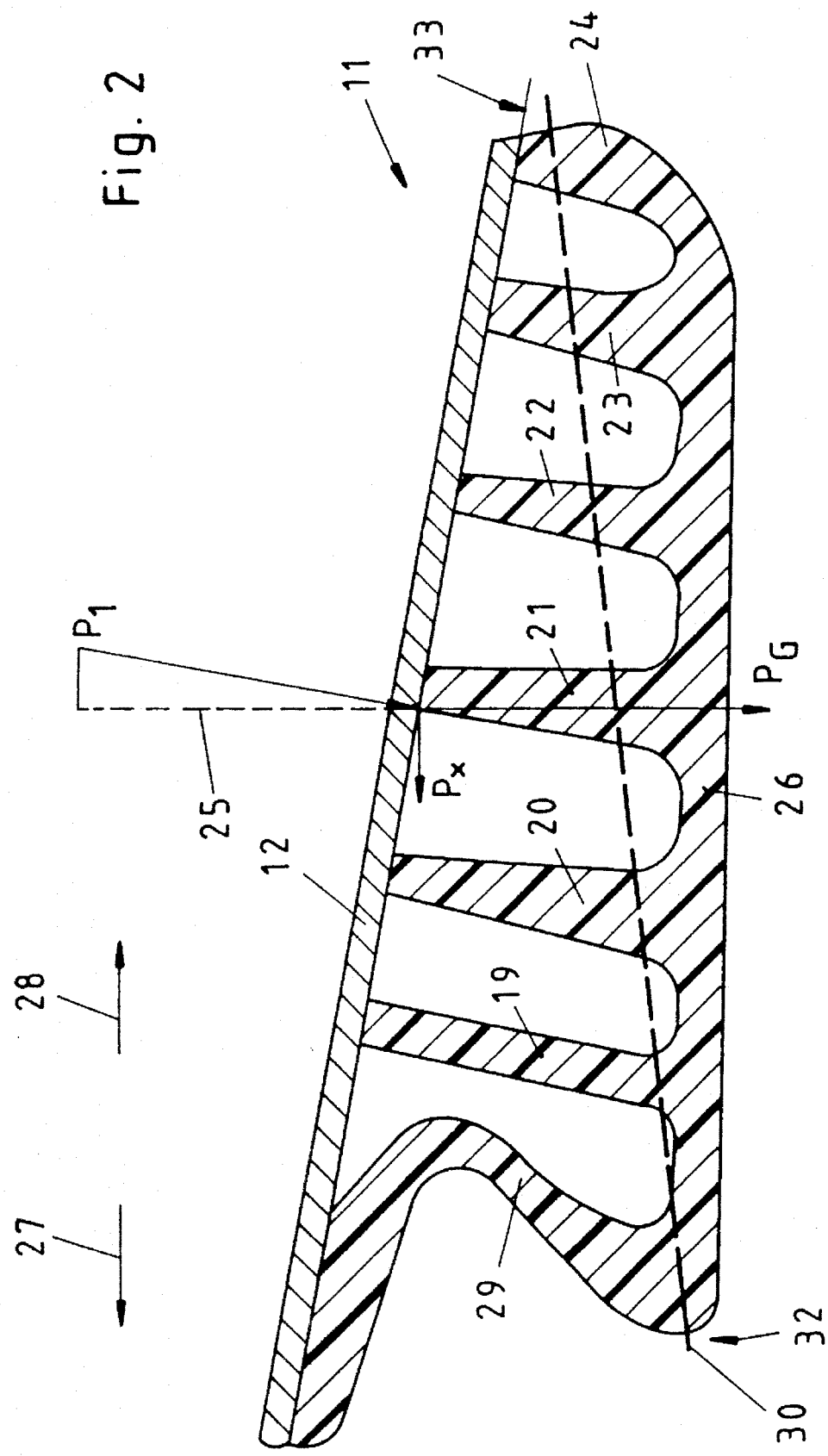

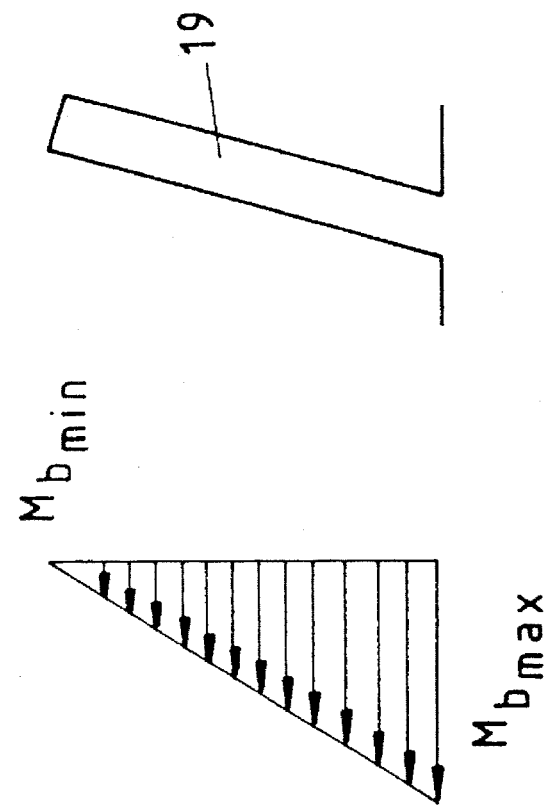
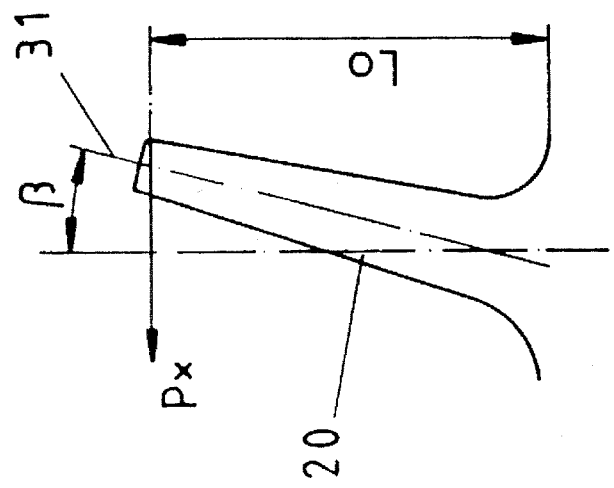

FOREFOOT RELIEF SHOE

BACKGROUND OF THE INVENTION

1. Field of the Invention

The present invention relates to a forefoot relief shoe having a sole portion which is substantially triangular when seen from the side or in a vertical longitudinal section, whose thickness diminishes toward the rear and which terminates anteriorly before the metatarsal region of the wearer.

2. Description of the Related Art

Such a forefoot relieving shoe is known from the U.S. Pat. No. 4,546,557.

Surgical interventions within the forefoot region, more particularly in the case of hallux valgus operations, call for a postoperative rest of the forefoot which is not strong enough as yet. If the patient does not wish to walk on crutches during this period, the relief shoes stated in the beginning can be used. This relief shoe has a tilted foot bed which, in connection with the sole portion terminating before the metatarsal region, ensures that the patient is able to put his foot down without straining the forefoot and also to roll off the same. The shoe according to the quoted U.S. patent is provided with a compressible sole possessing a compressibility which increases from the rear toward the front. This construction is intended to provide a better absorption within the forward area of the shoe.

The technical problem of the present invention is to develop the shoe further to the effect that it is made possible for the same to be worn over longer periods of time or for longer periods of use without any resultant damage to the walking block. In this case it is intended to ensure as good as possible a wearing comfort.

SUMMARY OF THE INVENTION

This technical problem is resolved by the forefoot relief. According to the invention, the sole portion of the relief shoe is provided with a hollow section having substantially vertical supports for the connection of the base constructed so as to cover the entire surface area and the upper body likewise of a construction covering the entire surface area and adjacent to the foot bed. At least within the central area, the supports, in the longitudinal axis direction toward the base, possess an increasing diameter or an increasing horizontal cross-section.

It has been shown that a homogeneous sole portion block or foamed material block is unsuitable for the rolling off function since excessive shearing forces are transmitted hereby to the hip joint. Shearing and rolling off forces act in a semi-elastic manner upon the sole portion, which ensures an adequate or improved service life of the forefoot relief shoe when a horizontal elasticity is given.

The supports preferably possess a truncated cylinder configuration, i.e. they enlarge conically in the downward direction. The central longitudinal axis of the individual supports is inclined toward the rear by an angle ranging between 10° and 20°, that is to say by an angle at which the supports are disposed substantially vertically in relation to the foot bed of the relief shoe or to the sole portion upper body of the same. The longitudinal axis of this upper body (or of the foot bed) is inclined by 5° through 15 relative to the horizontal or to the base.

In order to improve the shock absorption, the front end wall is bent in an S-like fashion in a longitudinal cross-sectional view. According to another construction of the invention, the support adjacent to the front end wall possesses over its entire length a constant cross-section (from the top downwardly). With this it is taken into account that the greatest proneness to fracture of the relief shoe did exist approximately within the central area of the sole portion so that a strengthening of the supports in the downward direction in the front area is not necessary. By preference, the supports extend over the respective full width of the sole, i.e. from side wall to side wall, whereby, in the form of partitions, they separate individual consecutively disposed cavities from each other. The thusly constructed cavity section, when compared with a solid section, is more enduringly elastic, saves material and is accordingly lighter.

In order to physiologically improve the walking sequence of the wearer from the instant when the heel touches the ground up to the front rolling off edge, according to a further construction of the invention, by the selection of the material and/or the geometrical design of the supports, the elasticity (softness) is designed so as to increase toward the rear, i.e. in the direction of the heel region. Due to the soft correction of the rear portion, an attenuation which decreases toward the rolling off process is produced when the heel is put onto the ground, whereby the circumstance is taken into consideration that, during the rolling off process, a high degree of stability is required in the front portion. It is advantageously ensured hereby that, in the course of the rolling off process, the toes are more fully protected against a ground contact than is the case with a solid section.

BRIEF DESCRIPTION OF THE DRAWINGS

An embodiment of the invention is depicted in the drawings. Thus

FIG. 1 shows a schematic side view of a forefoot relief shoe;

FIG. 2 shoes a detailed view of this relief shoe within the area of the sole portion;

FIGS. 3a, 3c each show a support according to the construction as per FIG. 2; and FIG. 3b shows a torque diagram along the longitudinal axis of the support according to FIG. 3a;

DETAILED DESCRIPTION OF THE PREFERRED EMBODIMENT

Figure 4:
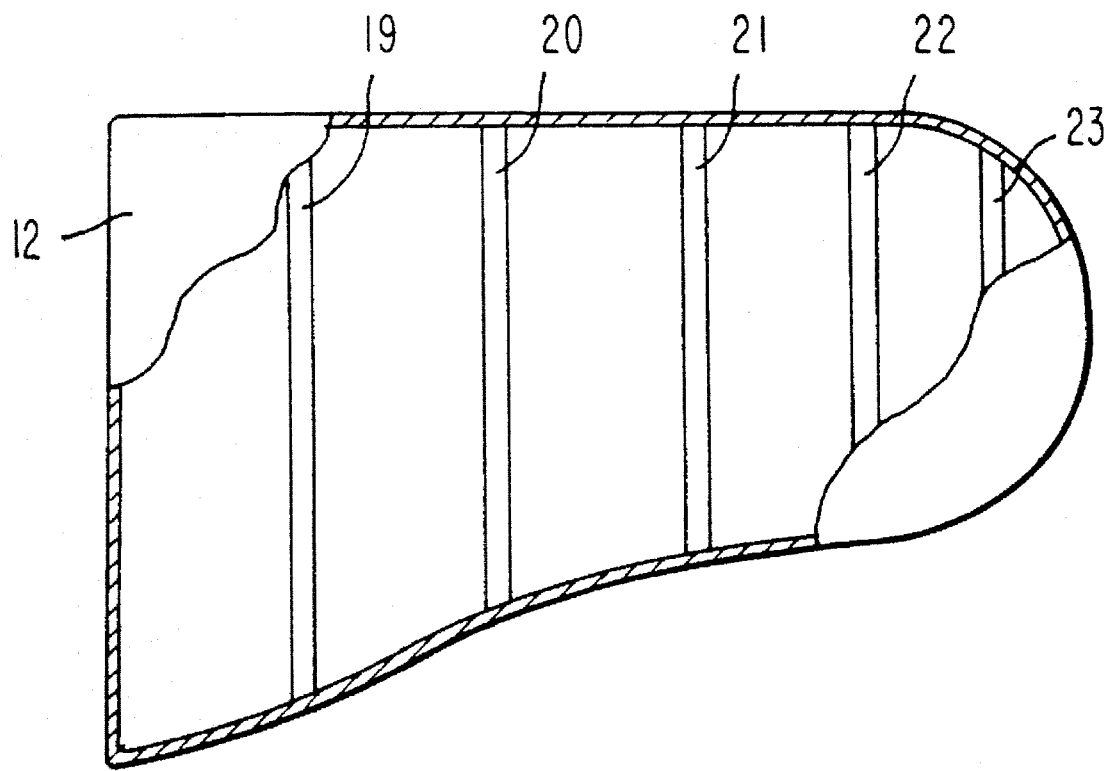
FIG. 4 is a top view of the sole portion, with a part of the upper body of the sole portion being broken away.

The forefoot relief shoe 10 is comprised essentially of a sole portion 11 and, if necessary, of an intermediate portion or upper body 12, which may form part of a foot bed 13, as well as of a part comprised of two shells 14 connected with the upper body or the foot bed, which may, by way of example, be closed with the aid of Velcro closing strips 15. The shells 14 can be of leather, plastic or textile fabric. The forefoot relief shoe is configured in such a way that the forefoot 16 is exposed and raised in the direction of the point of the foot, which is brought about by the substantially triangular contour of the sole portion 11. The angle of inclination $\simeq$ ranges regularly between 5° and 15°. The foot bed 13 terminates with its front point 17 before the metatarsal region which must not be subjected to any load. When walking, the wearer of the relief shoe 10 is able to put down the shoe first of all within the region of the heel 18 and to roll off in the forward direction without having to run the risk of touching the ground with the forefoot or the toes.

However, differently from embodiments according to the state of the art, the sole portion 11 is not constructed in the form of a homogeneous body, but possesses a honeycomb-like hollow sectional structure 24 with vertical supports 19 through 23. As shown in FIG. 4 of the drawing, the vertical supports 19 through 23 may extend over the entire width of the sole portion 11. At least within the central area, i.e. within the area of the median perpendicular 25, the supports 20, 21, 22 and 23 are constructed in such a way that they possess an increasing diameter or an increasing horizontal area cross-section in the longitudinal axial direction toward the base 26. The cross-sectional increase of the upper body 12 up to the base 26 increases the service life of the sole portion 11 because of it being possible to counter the shearing forces 27 and the rolling off forces 28, respectively, with a greater elasticity. Forces P acting upon the foot bed under Index I are divided according to the force parallelogram into shearing forces P under Index X and downwardly acting forces P under Index G. By means of the construction according to the invention, the pliability of the sole portion 11 is increased within the area of greater shearing or rolling off forces or the material within the areas close to the ground is strengthened by the absorption of the vertical forces by the supports. When viewed across its length, the front support 19 may be constructed so as to be uniformly thick or wide since, close to the forefoot, the forces—differently from within the heel region—are greater. The front end wall 29 is bent in an S-like fashion for the sake of the shock absorption and a better pliability.

Figure 5:
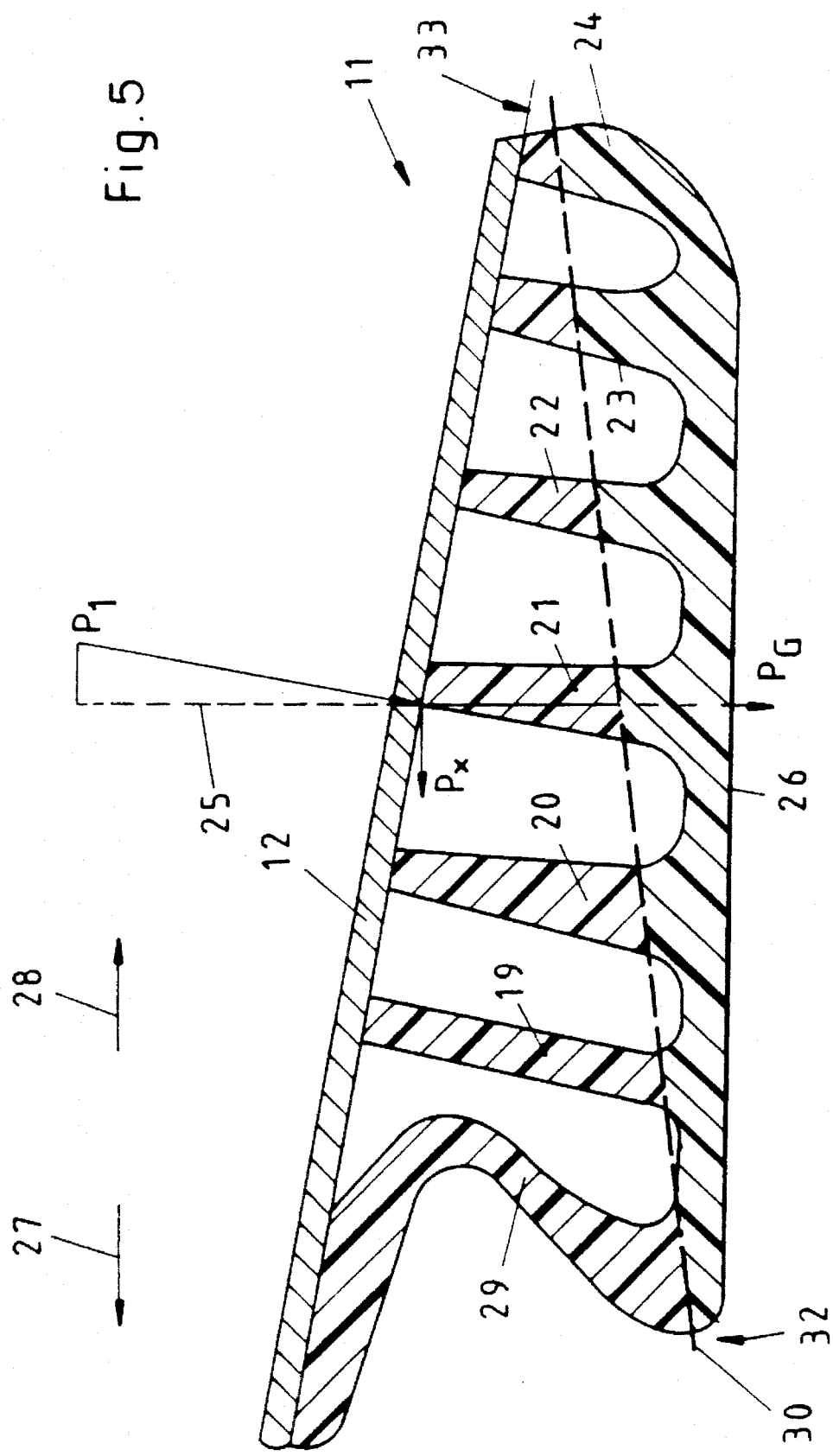
FIGS. 5 and 6 are sectional views, similar to FIG. 2, showing additional embodiments of the relief shoe according to the present invention.
Figure 6:
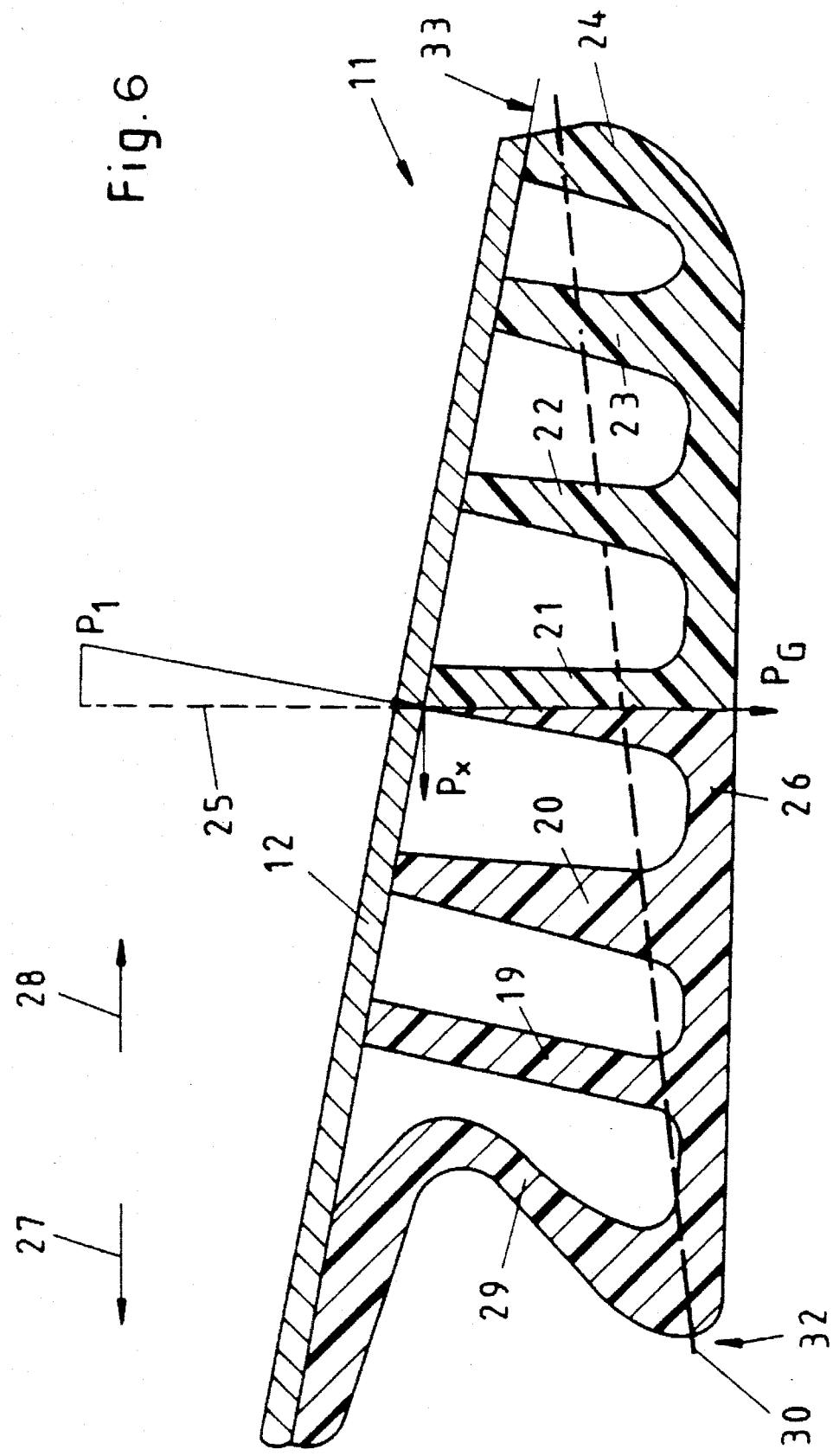

In order to enhance the walking or wearing comfort, as shown in FIG. 5, above the diagonal plane 30, a harder material, i.e. a material possessing a great elasticity constant and, within the area located therebelow, a soft material possessing a lower elasticity constant, is employed. As shown in FIG. 6, the front part of the base 26 including the supports attached thereto and the rear part of the base 26 and the supports attached thereto are of different materials. Preferably, the material of the rear part is softer than the material of the front part.

As is clearly shown in FIG. 3a, the support 20 is in a corresponding manner as all the other supports 19 through 23, inclined toward the rear, in which case their longitudinal axis 31 with a vertical forms an angle β of between 10° and 20°. The torques acting along the support which result according to the correlation N under Index B=P under Index X×L, are illustrated in FIG. 3b. From this it becomes clear that the torque stress increases from the top toward the bottom in the horizontal direction. In a corresponding manner the cross-section of the support is also increased. Where the acting torques are less powerful, viz. in the proximity of the forefoot region, the construction as per the FIG. 3c can be chosen.

What is claimed is:

1. A forefoot relief shoe comprising a sole portion having a front and a rear, the sole portion further having a longitudinal direction and a thickness, the sole portion having a triangular shape in the longitudinal direction, wherein the thickness of the sole portion decreases toward the rear, the front of the sole portion ending short of the metatarsal region of the foot of the wearer of the relief shoe, the sole portion comprising a plate-shaped base and a plate-shaped upper body attached to a foot bed, and upwardly extending supports connecting the base and the upper body, the supports extending transversely of the longitudinal direction, wherein, at least in a middle part of the sole portion, the supports have a thickness which increases toward the base, and wherein each support has a central longitudinal axis which is inclined rearwardly relative to the vertical by an angle of between 10° and 20°.

2. The forefoot relief shoe according to claim 1, wherein each support is truncated cylinder-shaped.

3. The forefoot relief shoe according to claim 1, wherein the upper body has a longitudinal axis which is inclined relative to the base by an angle of between 5° and 15°.

4. The forefoot relief shoe according to claim 1, wherein the front of the sole portion is S-shaped.

5. The forefoot relief shoe according to claim 1, wherein the supports include a support adjacent to the front of the sole portion, the support adjacent to the front of the sole portion having a constant thickness.

6. The forefoot relief shoe according to claim 1, wherein the sole portion has a width, the supports extending over the entire width of the sole portion.

7. The forefoot relief shoe according to claim 1, wherein the sole portion is of a material whose softness increases toward the rear.

8. The forefoot relief shoe according to claim 1, wherein the sole portion is of a different material above and below a diagonal plane extending from the base at the front to an upper edge of the rear of the sole portion, the material above the diagonal being harder than the material below the diagonal plane.

* * * * *